(12) United States Patent
Catinat et al.

(10) Patent No.: US 6,380,407 B1
(45) Date of Patent: Apr. 30, 2002

(54) METHOD FOR MAKING AN OXIRANE

(75) Inventors: Jean-Pierre Catinat, Waudrez; Michel Strebelle, Brussels, both of (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 09/646,787

(22) PCT Filed: Mar. 20, 1999

(86) PCT No.: PCT/EP99/01956

§ 371 Date: Sep. 22, 2000

§ 102(e) Date: Sep. 22, 2000

(87) PCT Pub. No.: WO99/48883

PCT Pub. Date: Sep. 30, 1999

(30) Foreign Application Priority Data

Mar. 24, 1998 (BE) ................................ 9800232

(51) Int. Cl.⁷ ...................... C07D 301/12; C07D 303/00
(52) U.S. Cl. ........................ 549/531; 549/512
(58) Field of Search .................................. 549/512, 531

(56) References Cited

U.S. PATENT DOCUMENTS 4,824,976 A * 4/1989 Clerici et al. ................ 549/529
4,937,216 A * 6/1990 Clerici et al. ................. 502/62

FOREIGN PATENT DOCUMENTS

EP        0 230 949 A2    8/1987

* cited by examiner

*Primary Examiner*—T. A. Solola
*Assistant Examiner*—Ebenezer Sackey
(74) *Attorney, Agent, or Firm*—Larson & Taylor PLC

(57) ABSTRACT

Continuous process for manufacturing an epoxide, according to which an olefin is reacted, in a reactor in the liquid phase, with a peroxide compound in the presence of a zeolite-based catalyst and in the presence of a solvent, and a gaseous compound is introduced continuously into the reactor at a flow rate which is sufficient to entrain at least some of the epoxide produced, which is recovered with the gaseous compound at the point at which it leaves the reactor.

17 Claims, 1 Drawing Sheet

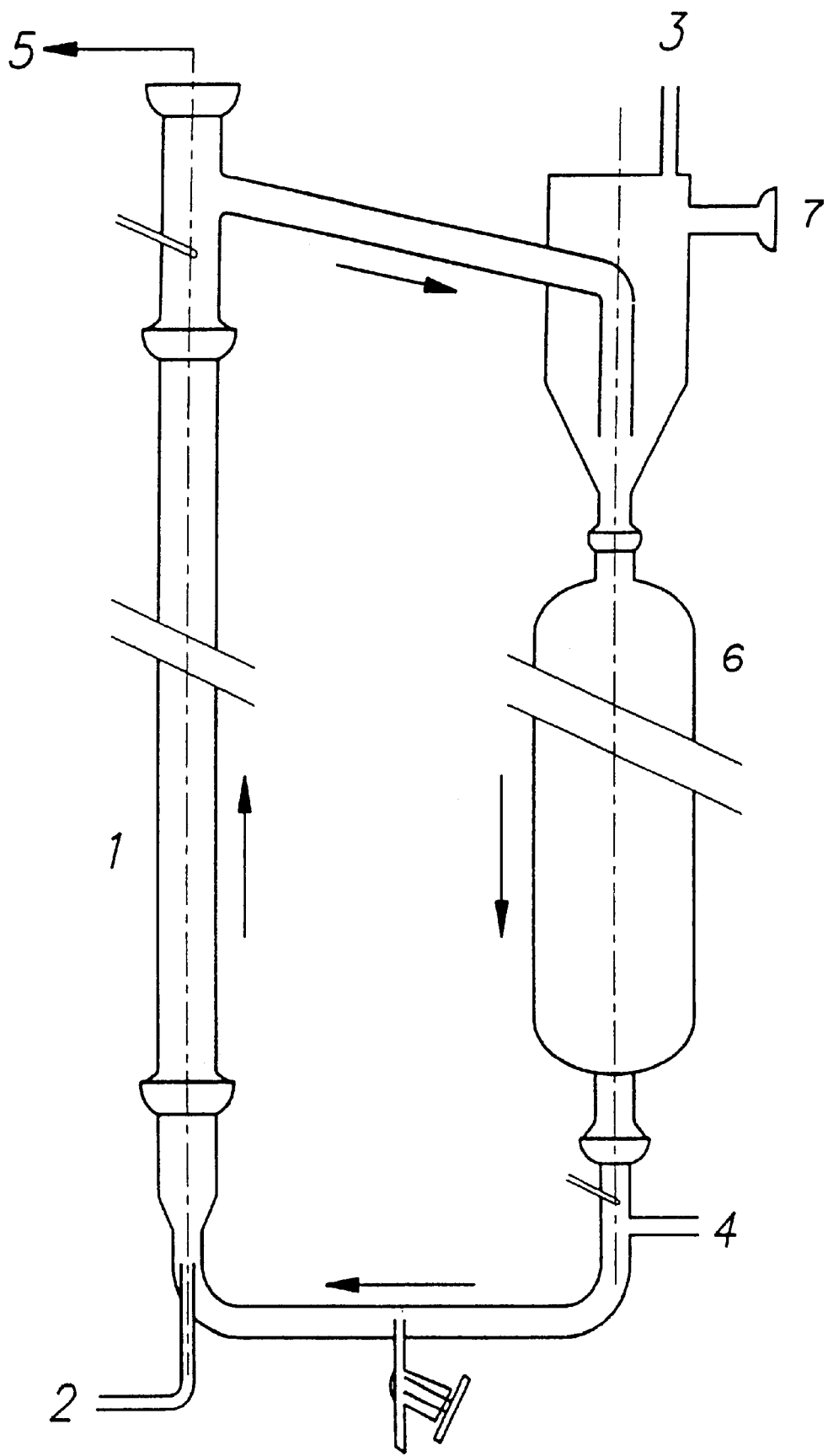

METHOD FOR MAKING AN OXIRANE

FIELD OF THE INVENTION

This appl. is a 371 of PCT/EP 99/01956 filed Mar. 20, 1999.

The invention relates to a process for manufacturing an epoxide by reaction between an olefin and a peroxide compound in the presence of a zeolite-based catalyst. The invention relates more particularly to a process for manufacturing 1,2-epoxypropane (or propylene oxide) by reaction between propylene and hydrogen peroxide.

BACKGROUND OF THE INVENTION

It is known practice to manufacture propylene oxide by epoxidation of propylene using hydrogen peroxide in the presence of a catalyst of the type TS-1, as described, for example, in patent application EP 0,230,949. This known process has the drawback of leading, under certain conditions, to low selectivities.

SUMMARY OF THE INVENTION

The invention is directed towards overcoming this drawback by providing a process for manufacturing an epoxide which is of high selectivity.

The invention consequently relates to a continuous process for manufacturing an epoxide, according to which an olefin is reacted, in a reactor in the liquid phase, with a peroxide compound in the presence of a zeolite-based catalyst and in the presence of a solvent, and a gaseous compound is introduced continuously into the reactor at a flow rate which is sufficient to entrain at least some of the epoxide produced, which is recovered with the gaseous compound at the point at which it leaves the reactor.

One of the essential characteristics of the invention lies in the introduction of a gaseous compound into the reactor. The reason for this is that it has been observed that the epoxide reacts in the epoxidation reaction medium with the water and the solvent to form by-products which reduce the selectivity of the epoxidation reaction. It has now been found that by introducing a gaseous compound into the reaction medium at a flow rate which is sufficient to allow the epoxide produced to be entrained and to remove it from the reactor at the same time as the gaseous compound, the contact time between the epoxide produced and the epoxidation reaction medium is reduced. The formation of by-products is thus avoided and the selectivity of the epoxidation is increased.

The function of the gaseous compound is to entrain the epoxide produced out of the reaction medium in order to prevent the epoxide from remaining in contact with the reaction medium for too long, and thus to avoid the formation of by-products. In other words, the gaseous compound allows the epoxide produced to be removed from the reaction medium by stripping.

The gaseous compound used in the process according to the invention can be any compound which is in gaseous form under the epoxidation conditions and which has no negative influence on the epoxidation reaction. It can be chosen from inert gases such as nitrogen.

One advantageous embodiment of the process according to the invention consists in introducing, into the reactor, the olefin in gaseous form and in a large excess such that the gaseous olefin can act, partially or completely, as the gaseous compound, i.e. it can entrain the epoxide produced and remove it from the reactor.

Another specific embodiment of the process according to the invention consists in introducing the gaseous compound into the reactor at a flow rate such that it makes it possible not only to entrain at least some of the epoxide produced, but also to circulate the liquid phase in the reactor, in particular when this reactor is a loop-type reactor.

BRIEF DESCRIPTION OF THE DRAWING

FIG. 1 shows a schematic view of a loop-type reactor using the process of the invention.

DETAILED DESCRIPTION OF THE PREFERRED EMBODIMENTS

In the process according to the invention, the gaseous compound is generally introduced into the reactor at a flow rate such that the ratio of the flow rate of the gaseous compound to the flow rate of supply of the peroxide compound is at least 5, in particular at least 8, values of at least 10 being common. The ratio of these flow rates is generally less than or equal to 50, in particular less than or equal to 30, values of less than or equal to 20 being common.

Any type of reactor, in particular a loop-type reactor, can be used in the process according to the invention. Bubble-siphon loop-type reactors, in which the circulation of the liquid and also optionally of the catalyst is obtained by bubbling a gas into one of the branches, are suitable for use. An example of such a reactor is shown schematically in the figure. The gaseous compound (preferably the olefin) is introduced into the bottom of the reaction zone 1 via the pipe 2. The other reagents (peroxide compound, solvent, catalyst, optionally one or more additives) are introduced into the reactor via the pipes 3 and 4. The liquid phase circulates in the reactor in the direction of the arrows. The gaseous compound rises in the reaction zone 1 and thus entrains the epoxide produced therein. A mixture of the gaseous compound and of epoxide produced leaves the reactor via the pipe 5. The liquid phase leaving from the top of the reaction zone 1 is recycled into the bottom of the reaction zone via a heat exchanger 6. The overflow of the liquid phase, which is depleted in propylene oxide by means of stripping, is carried out via the pipe 7. A reactor comprising two concentric zones, the central zone providing the function of zone 1 of the reactor shown schematically in the figure, and the peripheral zone providing the function of zone 6 of the reactor shown schematically in the figure, can also be used in the process according to the invention.

In the process according to the invention, it may prove advantageous to maintain the pH of the liquid phase during the reaction between the olefin and the peroxide compound at a value of at least 4.8, in particular of at least 5. The pH is advantageously less than or equal to 6.5, in particular less than or equal to 6. Good results are obtained when the pH is from 4.8 to 6.5, preferably from 5 to 6. The pH of the liquid phase during the epoxidation reaction can be controlled by addition of a base. This base can be chosen from water-soluble bases. These can be strong bases. As examples of strong bases, mention may be made of NaOH and KOH. They can also be weak bases. The weak bases can be inorganic. As examples of weak inorganic bases, mention may be made of $NH_4OH$, $Na_2CO_3$, $NaHCO_3$, $Na_2HPO_4$, $K_2CO_3$, $Li_2CO_3$, $KHCO_3$, $LiHCO_3$ and $K_2HPO_4$. The weak bases can also be organic. Weak organic bases which may be suitable are the alkali metal or alkaline-earth metal salts of carboxylic acids preferably containing from 1 to 10 carbon atoms. Sodium acetate may be mentioned by way of example. Weak bases give good results. Weak organic bases are preferred. Sodium acetate is particularly suitable.

The peroxide compounds which can be used in the process according to the invention are peroxide compounds containing active oxygen which are capable of carrying out an epoxidation. Hydrogen peroxide and peroxide compounds which can produce hydrogen peroxide under the epoxidation reaction conditions are suitable for use. Hydrogen peroxide is preferred.

In the process according to the invention, the peroxide compound is generally used in an amount of at least 1 mol per kg of liquid phase, in particular at least 1.5 mol per kg of liquid phase. The amount of peroxide compound is generally less than 10 mol per kg of reaction medium; it is usually less than or equal to 5 mol per kg of liquid phase, in particular less than or equal to 3 mol per kg of liquid phase.

In the process according to the invention, the peroxide compound is advantageously used in the form of an aqueous solution. In general, the aqueous solution contains at least 10% by weight of peroxide compound, in particular at least 20% by weight. It usually contains not more than 70% by weight of peroxide compound, in particular 50% by weight.

In the process according to the invention, the olefin reacts with the peroxide compound in the presence of the catalyst and the solvent at a temperature which is generally at least 0° C., in particular at least 20° C. The temperature is generally less than 150° C.; it is usually less than or equal to 70° C., in particular less than or equal to 40° C.

In the process according to the invention, the reaction between the olefin and the peroxide compound can take place at atmospheric pressure. It can also take place under pressure. Generally, this pressure does not exceed 40 bar. A pressure of 20 bar is suitable in practice.

The catalysts used in the process according to the invention contain a zeolite, i.e. a solid containing silica which has a microporous crystalline structure. The zeolite is advantageously free of aluminum. It preferably contains titanium.

The zeolite which can be used in the process according to the invention can have a crystalline structure of ZSM-5, ZSM-11, MCM-41 type or of beta-zeolite type. Zeolites of ZSM-5 type are suitable for use. Those with an infrared absorption band at about 950–960 cm$^{-1}$ are preferred.

The zeolites which are particularly suitable are the titanium silicalites. Those corresponding to the formula $xTiO_2 (1-x)SiO_2$ in which x is from 0.0001 to 0.5, preferably from 0.001 to 0.05, give good performance. Materials of this type, known under the name TS-1 and having a crystalline structure of ZSM-5 type, give particularly favourable results.

The epoxide which can be prepared by the process according to the invention is an organic compound comprising a group corresponding to the general formula:

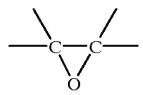

The epoxide generally contains from 2 to 20 carbon atoms, preferably from 3 to 10 carbon atoms. An epoxide which can be prepared advantageously by the process according to the invention is a 1,2-epoxypropane.

The olefins which are suitable in the process according to the invention contain from 3 to 10 carbon atoms. Propylene is preferred.

Solvents which can be used in the process according to the invention can be aliphatic organic derivatives containing from 1 to 4 carbon atoms. Methanol can be mentioned by way of example.

The initial content of peroxide compounds in the liquid phase is generally between 0.1 and 10 mol/kg. It is preferably between 1.5 and 3 mol/kg.

EXAMPLE 1 AND 2

Propylene oxide was manufactured in a bubble-siphon reactor as shown schematically in FIG. 1, by reaction between propylene and 35% hydrogen peroxide in the presence of methanol and 5.25 g of catalyst TS-1, used in the form of beads 0.5 mm in diameter.

The tests were carried out at a temperature of 35° C., with a continuous supply of hydrogen peroxide at a flow rate of 0.57 mol/h. The amount of methanol used was 16 mol/mol of $H_2O_2$. In Example 1, 75 l/h (s.t.p) of propylene (i.e. 3.3 mol/h) were injected. In Example 2, 250 l/h (s.t.p) of propylene (i.e. 11.2 mol/h) were injected. At these flow rates, the introduction of propylene into the reactor caused circulation of the liquid reaction medium and of the catalyst in suspension.

In Example 1, a selectivity towards propylene oxide of 83% and a degree of conversion of the $H_2O_2$, after reaction for 500 hours, of 76% were obtained.

In Example 2, a selectivity towards propylene oxide of 90% and a degree of conversion of the $H_2O_2$, after reaction for 500 hours, of 79% were obtained.

(The selectivity towards propylene oxide is given by the molar ratio, expressed as a percentage, between the amount of propylene oxide obtained divided by the sum of all of the organic products formed).

EXAMPLE 3

Propylene oxide was manufactured in a loop reactor similar to the one shown schematically in FIG. 1, by reaction between propylene and 35% hydrogen peroxide in the presence of methanol and of 8.24 g of catalyst TS-1 bound to a honeycomb support.

The tests were carried out at a temperature of 35° C., with a continuous supply of hydrogen peroxide at a flow rate of 0.5 mol/h. The amount of methanol used was 16 mol/mol of $H_2O_2$. 120 l/h (s.t.p) of propylene and 140 l/h (s.t.p) of nitrogen were injected.

A selectivity towards propylene oxide of 89% and a degree of conversion of the $H_2O_2$, after reaction for 1 hour, of 60% were obtained.

EXAMPLE 4

Propylene oxide was manufactured in a bubble-siphon reactor as shown schematically in FIG. 1, by reaction between propylene and 40% hydrogen peroxide in the presence of methanol and 5.25 g of catalyst TS-1, used in the form of beads 0.5 mm in diameter.

The tests were carried out at a temperature of 56° C., with a continuous supply of hydrogen peroxide at a flow rate of 0.57 mol/h. The flow rate of propylene is 250 l/h (s.t.p).

In a 1st test, the initial concentration of $H_2O_2$ in the reaction medium (i.e. in the absence of reaction) is set at 2 mol $H_2O_2$/kg of liquid phase, which, taking the stripping of the $CH_3OH$ into account, corresponds to a $CH_3OH/H_2O_2$ ratio in the reaction medium in the absence of reaction equal to 13 mol/mol.

In a 2nd test, the initial concentration of $H_2O_2$ in the reaction medium (i.e. in the absence of reaction) was brought to 6.5 mol $H_2O_2$/kg of liquid phase, by simply reducing the flow rate of methanol used relative to the 1st test, from 759 to 375 ml/h. The $CH_3OH/H_2O_2$ ratio in the reaction medium, in the absence of reaction and taking the stripping of the $CH_3OH$ into account, is close to 2.9 mol/mol under these conditions.

In a 3rd test, the flow rate of methanol used was reduced to 210 ml/h. Taking the stripping of the $CH_3OH$ into account, the initial concentration of $H_2O_2$ thus goes to 11.4 mol $H_2O_2$/kg of liquid phase and the $CH_3OH/H_2O_2$ ratio in the reaction medium, in the absence of reaction, goes to 1.3 mol/mol.

After testing for 6 h, the degrees of conversion of the $H_2O_2$ for the 1st, 2nd and 3rd tests are, respectively, 69, 73 and 70%, and the selectivities towards propylene oxide are, respectively, equal to 83, 85 and 89%.

What is claimed is:

1. A continuous process for manufacturing an epoxide, according to which an olefin is reacted, in a reactor in the liquid phase, with a peroxide compound in the presence of a zeolite-based catalyst and in the presence of a solvent, and a gaseous compound is introduced continuously into the reactor at a flow rate which is sufficient to entrain some of the epoxide produced, which is recovered with the gaseous compound at the point at which it leaves the reactor.

2. The process according to claim 1, wherein the olefin is introduced into the reactor in gaseous form in a large excess, such that the olefin acts as a reactant and as the gaseous compound.

3. The process according to claim 1, wherein the reactor is a loop reactor.

4. The process according to claim 3, wherein the gaseous compound flows through the reactor at a rate sufficient to circulate the liquid phase in the loop reactor.

5. The process according to claim 1, wherein the ratio of the flow rate of the gaseous compound to the flow rate of supply of the peroxide compound is greater than or equal to 5.

6. The process according to claim 1, wherein the reactor is bubble-siphon loop type.

7. The process according to claim 1, wherein the pH of the liquid phase is maintained at from 4.8 to 6.5 by addition of a base to the liquid phase.

8. The process according to claim 1, wherein the peroxide compound is used in an amount of from 1 to 10 mol per kg of liquid phase, and wherein the peroxide compound is used in the form of an aqueous solution containing from 10 to 70% of peroxide compound.

9. The process according to claim 1, wherein the temperature at which the olefin reacts with the peroxide compound in the presence of the catalyst and the solvent is from 0 to 150° C.

10. The process according to claim 1, wherein zeolite is titanium silicalite.

11. The process according to claim 1, wherein the epoxide is 1,2-epoxypropane, the olefin is propylene, the peroxide compound is hydrogen peroxide, the solvent is methanol and the gaseous compound is propylene.

12. The process according to claim 5 wherein the ratio of the flow rate of the gaseous compound to the flow rate of supply of the peroxide compound is greater than or equal to 10.

13. The process according to claim 8 wherein the peroxide compound is used in an amount from 1.5 to 5 mol per kg of liquid phase.

14. The process according to claim 8 wherein the peroxide compound is used in the form of an aqueous solution containing from 20 to 50% of peroxide compound.

15. The process according to claim 9 wherein the temperature at which the olefin reacts with the peroxide compound in the presence of the catalyst and the solvent is from 0 to 70° C.

16. The process according to claim 15 wherein the temperature at which the olefin reacts with the peroxide compound in the presence of the catalyst and the solvent is from 20 to 40° C.

17. The process according to claim 10 wherein the titanium silicalite is of TS-1 type having a crystalline structure ZSM-5 type.

* * * * *